United States Patent [19]

Cucuiat et al.

[11] 4,429,572

[45] Feb. 7, 1984

[54] METHOD AND APPARATUS FOR THE DETERMINATION OF THE DENSITY OF LIGHT HYDROCARBONS MIXTURES

[75] Inventors: Iuliu M. Cucuiat; Gabriel Holdis; Valentin E. Hanciulescu, all of Cîmpina, Romania

[73] Assignee: Institutul de Cercetari si Proiectari Pentru Petrol si Gaze, Cîmpinia, Romania

[21] Appl. No.: 289,145

[22] Filed: Aug. 3, 1981

[51] Int. Cl.³ .............................................. G01N 9/04
[52] U.S. Cl. ........................................ 73/433; 73/32 R
[58] Field of Search .............. 73/433, 32 R, 434, 435, 73/436, 437; 374/54, 45, 49

[56] References Cited

U.S. PATENT DOCUMENTS

| | | | |
|---|---|---|---|
| 1,222,919 | 4/1917 | Bennet | 73/433 |
| 2,270,699 | 1/1942 | Davis | 73/32 R |
| 3,229,503 | 1/1966 | Poole et al. | 73/32 R |
| 3,572,094 | 4/1969 | Banks | 73/32 R X |
| 4,301,676 | 11/1981 | Gokcen | 374/45 X |

FOREIGN PATENT DOCUMENTS

| | | | |
|---|---|---|---|
| 2816495 | 11/1979 | Fed. Rep. of Germany | 73/433 |
| 174419 | 12/1965 | U.S.S.R. | 73/32 R |

OTHER PUBLICATIONS

Dauphinee et al., "A New Automated Laboratory Salinometer" Sea Technology, vol. 16, No. 3, pp. 23-25, Mar. 1975.

Primary Examiner—Anthony V. Ciarlante
Assistant Examiner—Tom Noland
Attorney, Agent, or Firm—Karl F. Ross; Herbert Dubno

[57] ABSTRACT

A method and an apparatus are disclosed for the determination of the density of a light hydrocarbon mixture by thermostatting the light hydrocarbon mixture in a large thermostatted vessel at a temperature at which said mixture is liquid in said thermostatted vessel below a level thereof. The large thermostatted vessel is next connected to at least one small container of known mass and volume and thermostatted at said temperature. Then a portion of the thermostatted light hydrocarbon mixture is transferred from said large vessel to the liquid level to the small container until the small container is filled with the light hydrocarbon mixture in liquid form. Any vapors present within the small container are vented leaving behind a liquid light hydrocarbon mixture. The small container is then disconnected from the large thermostatted vessel and the mass of the small container and the light hydrocarbon mixture is determined. Once the mass of the light hydrocarbon mixture and the small container is determined, one can easily determine the mass of the light hydrocarbon mixture as well as its density at the thermostatic temperature.

2 Claims, 2 Drawing Figures

METHOD AND APPARATUS FOR THE DETERMINATION OF THE DENSITY OF LIGHT HYDROCARBONS MIXTURES

FIELD OF THE INVENTION

This invention relates to a method and an apparatus for the determination of the density of light hydrocarbon mixtures, ethane plus fractions and/or propane plus fractions, such as natural gasoline.

BACKGROUND OF THE INVENTION

There are known in the art methods for the determination of the density of light hydrocarbons mixtures which include the filling of a container having a known volume and a known weight with the light hydrocarbon mixtures by connecting the container to the product source, thereafter the container is thermostated and is weighed on an analytical balance.

The drawback of these methods is that the thermostating is done after the filling of the container with the light hydrocarbons mixture and this fact leads to an uncontrollable filling of the container.

There are known in the art apparatuses for the determination of the density of light hydrocarbon mixtures which include a container which comprises two chambers, one for work and another for compensation, the chambers being separated by a valve. After the filling of the working chamber with the light hydrocarbon mixture at the temperature equal to the environmental temperature, an inlet valve of the working chamber and another valve which controls the degree of filling with light hydrocarbon mixtures of the working chamber are closed. Thereafter the valve between the working chamber and the chamber of compensation is opened and the container is thermostated, the pressure of the light hydrocarbon mixture during the thermostatation being measured with a pressure gauge.

The drawbacks of these apparatuses are that they have a relatively complex construction and do not allow the simultaneous thermostating of two or more containers simultaneously filled with the light hydrocarbon mixture.

SUMMARY OF THE INVENTION

The method according to this invention eliminates the before mentioned drawback and comprises the following steps:

(a) the light hydrocarbon mixture is introduced into a thermostated cylindrical vessel, (b) thereafter connections are made up between said cylindrical vessel and some small containers, of which both the weight and the volume are known, in order to fill the small containers.

(c) filling the small containers, during the filling of the small containers with the light hydrocarbons mixture and thereafter until the thermal equilibrium is reached both the cylindrical vessel and the small containers being kept at the same temperature, (d) thereafter the small containers filled according to steps (b) and (c) are removed from the thermostated medium and, one by one, weighed on an analytical balance in order to determine of the density of the light hydrocarbon mixture at the temperature of the thermostated bath which was selected as the reference temperature.

During the filling of the small containers in steps (b) and (c), the position of the small containers is below that of the liquid level of the light hydrocarbon mixture from the said cylindrical vessel the level being seen by a glass gauge fixed on the cylindrical vessel. In such a manner, the small containers are full of liquid.

The apparatus, according to this invention, and which eliminates the before mentioned drawbacks, comprises a pressure-resistant cylindrical vessel, which may be thermostated, closed at one end by a cap, said cap containing a valve necessary to vacuum the vessel before the adding of the light hydrocarbon mixture; a pressure gauge and a pipe having at its upper end a valve for filling and emptying the vessel are connected; the pipe is introduced in the vessel in the vicinity of the other end of the vessel; on the vessel there are fixed two glass gauges which allow seeing the level of the liquid inside the vessel; the liquid (the light hydrocarbon mixture) may fill some small containers via some connection lines with valves which are opened; at the upper end the small containers have a special valve which allows the vapors to escape until the small containers are full of liquid; the other end of each of the small containers is connected by a valve located on the connection line between the cylindrical vessel and the small containers.

BRIEF DESCRIPTION OF THE DRAWING

A more complete understanding of the invention may be obtained by reference to the drawing in which.

SPECIFIC DESCRIPTION

Figure 1:
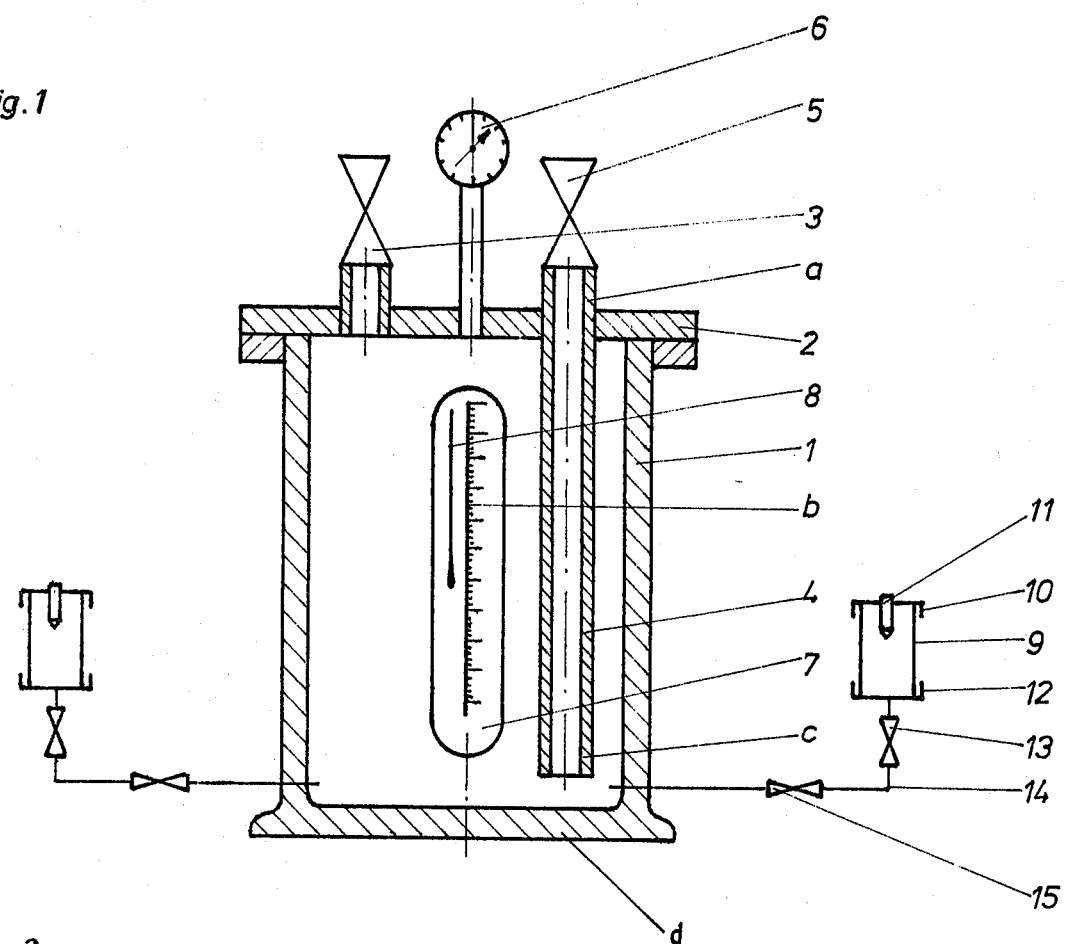
FIG. 1 is a longitudinal section of the apparatus.
Figure 2:
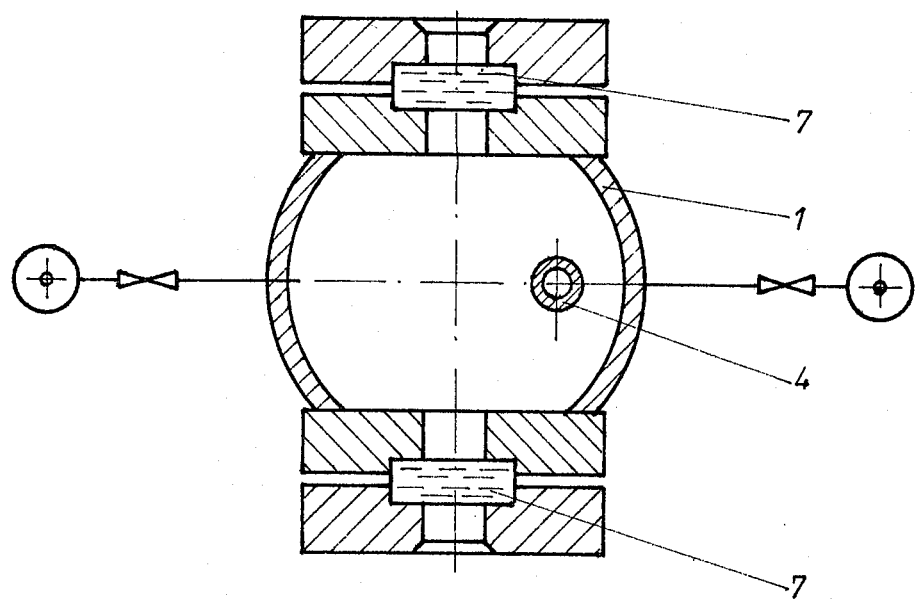
FIG. 2 is a transverse section of the apparatus.

The method according to this invention, comprises the following steps:

(a) the light hydrocarbons mixture (ethane plus fraction and/or propane plus fraction) is introduced into a thermostated cylindrical vessel, the value of the temperature of thermostated medium being selected as reference temperature, (b) thereafter connection is made between said cylindrical vessel and some small containers, which both the weight and the volume are known, in order to fill the small containers, (c) filling the small containers, during the filling of the small containers with the light hydrocarbon mixture and thereafter until thermal equilibrium is reached, both the cylindrical vessel and the small containers being kept at the same temperature, (d) thereafter the small containers filled according to steps (b) and (c) is removed from the thermostated medium and, one by one, weighed on an analytical balance in order to determine of the density of the light hydrocarbon mixture at the temperature value selected as reference temperature.

During the filling of the small containers, in steps (b) and (c) the position of the small containers is below that of the liquid level of the light hydrocarbons mixture from the said cylindrical vessel, the level being observable by a glass gauge fixed on the cylindrical vessel. In such a manner, the small containers are filled with liquid.

The apparatus, according with this invention comprises a stainless steel, pressure-resistant cylindrical vessel 1, closed at one end by a cap 2. In the cap 2 a valve 3 necessary to vacuum the cylindrical vessel and a pipe 4 having at its upper end a valve 5 for filling and emptying the vessel 1 with the light hydrocarbons mixture via the pipe 4.

In the cap 2 a pressure gauge 6 allows measuring the pressure inside the vessel 1. The vessel 1 is equipped with one or two glass gauges 7 having volume indicia "b" and which allow viewing the inside of the vessel 1.

In the vessel 1 a pressure areometer 8 for the determination of the specific gravity of the light hydrocarbon mixtures may be introduced.

For the determination of the density of the light hydrocarbon mixture introduced in the vessel 1 via the pipe 4 which has the lower end "c" in the vicinity of the wall "d" of the vessel 1, a part of the light hydrocarbons mixture is allowed to fill at least one small container 9 hermetically closed at its upper end by a cap 10. In the cap 10 there is fitted a thread plug 11 which allows the vapors to escape until the small container is full of liquid. At the down part of the small container another cap 12 and a valve 13 are connected.

Each small container 9 together with the valve 13 is cut-in and cut-off (after filling with the light hydrocarbon mixture and weighted on an analytical balance which is not represented in the figures) at and from a connection line 14 with the vessel 1. On the connection line 14 there is placed a valve 15.

The method and the apparatus according to the present invention have the following advantages:
allows the determination of the density of a sample of light hydrocarbon mixture at a reference temperature,
a simple construction,
working reliability.

We claim:

1. A method to aid in the determination of the density of a light hydrocarbon mixture which comprises the following steps:
   (a) thermostatting the light hydrocarbon mixture in a large thermostatted vessel at a temperature at which said mixture is liquid in said thermostatted vessel below a level of the surface of the liquid mixture;
   (b) connecting said large thermostatted vessel simultaneously to a plurality of small containers of known mass and of a known volume at said temperature;
   (c) transferring a portion of said thermostatted light hydrocarbon mixture from said large vessel below said level to said small containers until said small containers are filled with the light hydrocarbon mixture in liquid form, said small containers being thermostatted to said temperature;
   (d) venting any vapor present in said small containers during the filling to thereof ensure complete filling with the light hydrocarbon mixture entirely in liquid form;
   (e) disconnecting the small thermostatted containers from the large thermostatted vessel and determining the mass of the small containers and the light hydrocarbon mixture; and
   (f) relating the mass of the small containers and the light hydrocarbon mixture to the density of the light hydrocarbon mixture at a given reference temperature.

2. Am apparatus to aid in the determination of the density of a light hydrocarbon mixture at a given temperature, which comprises:
   (a) a large vessel thermostatted at a predetermined temperature at which a light hydrocarbon mixture can be received in a liquid form below a surface;
   (b) means for introducing the light hydrocarbon mixture into the large vessel including a pipe reaching downwardly below said surface; p1 (c) means for evacuating gas from said vessel above said surface;
   (d) means forming a window from viewing the level of said surface in said vessel;
   (e) a pressure gauge on said vessel for measuring the pressure of said light hydrocarbon moisture therein;
   (f) a plurality of small containers of known mass and volume thermostatted to said predetermined temperature;
   (g) means for detachably connecting said containers simultaneously to said vessel below said surface whereby said containers can be filled by a liquid from said vessel; and
   (h) a valve on each of said small containers for venting gases therefrom to ensure complete filling of the small containers with liquid from said vessel whereby weighing of said small containers will provide a value of the mass of the liquid therein such that the density of the liquid hydrocarbon mixture can be ascertained using the known volume of the small containers.

* * * * *